United States Patent [19]

Gluck

[11] Patent Number: 5,738,625
[45] Date of Patent: Apr. 14, 1998

[54] METHOD OF AND APPARATUS FOR MAGNETICALLY STIMULATING NEURAL CELLS

[76] Inventor: Daniel S. Gluck, 528 Sprague Rd., Penn Valley, Pa. 19072

[21] Appl. No.: 508,650

[22] Filed: Jul. 28, 1995

Related U.S. Application Data

[63] Continuation-in-part of Ser. No. 74,507, Jun. 11, 1993, abandoned.

[51] Int. Cl.$^6$ .................................................. A61N 2/00
[52] U.S. Cl. ............................................ 600/9; 128/897
[58] Field of Search ..................... 600/9–15; 128/897–8

[56] References Cited

U.S. PATENT DOCUMENTS

| | | |
|---|---|---|
| 3,918,461 | 11/1975 | Cooper . |
| 4,646,744 | 3/1987 | Capel . |
| 4,813,418 | 3/1989 | Harris . |
| 4,919,139 | 4/1990 | Brodard . |
| 4,940,453 | 7/1990 | Cadwell . |
| 4,977,895 | 12/1990 | Tannenbaum . |
| 5,047,005 | 9/1991 | Cadwell . |
| 5,061,234 | 10/1991 | Chaney . |
| 5,066,272 | 11/1991 | Eaton et al. . |
| 5,092,835 | 3/1992 | Schurig et al. . |
| 5,116,304 | 5/1992 | Cadwell . |
| 5,117,826 | 6/1992 | Bartelt et al. . |
| 5,224,922 | 7/1993 | Kurtz . |

OTHER PUBLICATIONS

Reilly, "Electrical Models for Neural Excitation Studies," *Johns Hopkins APL Technical Digest*, vol. 9, No. 1 1988, pp. 44–59.

Reilly,*Electrical Stimulation and Electropathology*, 1992, chapter 4, "Excitation Models".

Amassian et al., "Focal stimulation of human cerebral cortex with the magnetic coil: a comparison with electrical stimulation," *Electroencephalography and clinical Neurophysiology*, 1989, pp. 401–416.

Mills et al., "Magnetic brain stimulation with a double coil: the importance of coil orientation," *Electroencephalography and clinical Neurophysiology*, 85, 1992, pp. 17–21.

Cohen et al., "Effects of coil design on delivery of focal magnetic stimulation. Technical considerations," *Electroencephalography and clinical Neurophysiology*, 1990, 75, pp. 350–357.

S. Chokroverty et al., *Magnetic Stimulation in Clinical Neurophysiology*, 1990.

H. Eaton, "Electric field induced in a spherical volume conductor from arbitrary coils: application to magnetic stimulation and MEG," *Medical & Biological Engineering & Computing*, Jul. 1992, pp. 433–440.

H. Eaton, "Magnetic Nerve Stimulation," *Johns Hopkins AFL Technical Digest*, vol. 12, No. 2, 1991, pp. 153–158.

D. Cohen et al., "Developing a More Focal Magnetic Stimulator, Part I: Some Basic Principles," *Journal of Clinical Neurophysiology*, vol. 8, No. 1, 1991, pp. 102–111.

K. Yunokuchi et al., "Developing a More Focal Magnetic Stimulator, Part II: Fabricating Coils and Measuring Induced Current Distributions," *Journal of Clinical Neurophysiology*, vol. 8, No. 1, 1991, pp. 112–120.

J. Cadwell, *The Design and Applications of Cadwell Magnetic Coils*.

*Primary Examiner*—John P. Lacyk
*Attorney, Agent, or Firm*—Lowe, Price, LeBlanc & Becker

[57] ABSTRACT

A first energy field is applied to a neural cell to be stimulated from a polarized quiescent state to an active depolarized state. The first field changes the cell from the quiescent state so the cell transmembrane potential differs from both of the states. While the transmembrane potential differs from both the states a field including a cyclic magnetic component is applied to the cell. The cyclic magnetic component has a frequency and amplitude and is combined with effects from the first energy field such that each cycle of the cyclic magnetic component causes an incremental change in transmembrane potential of the cell without changing the cell from the quiescent to the active state. The cyclic magnetic component applied to the cell has a duration and amplitude and is combined with the effects of the first energy field to cause an accumulation of the incremental changes to change the cell state from the quiescent to the active state.

79 Claims, 7 Drawing Sheets

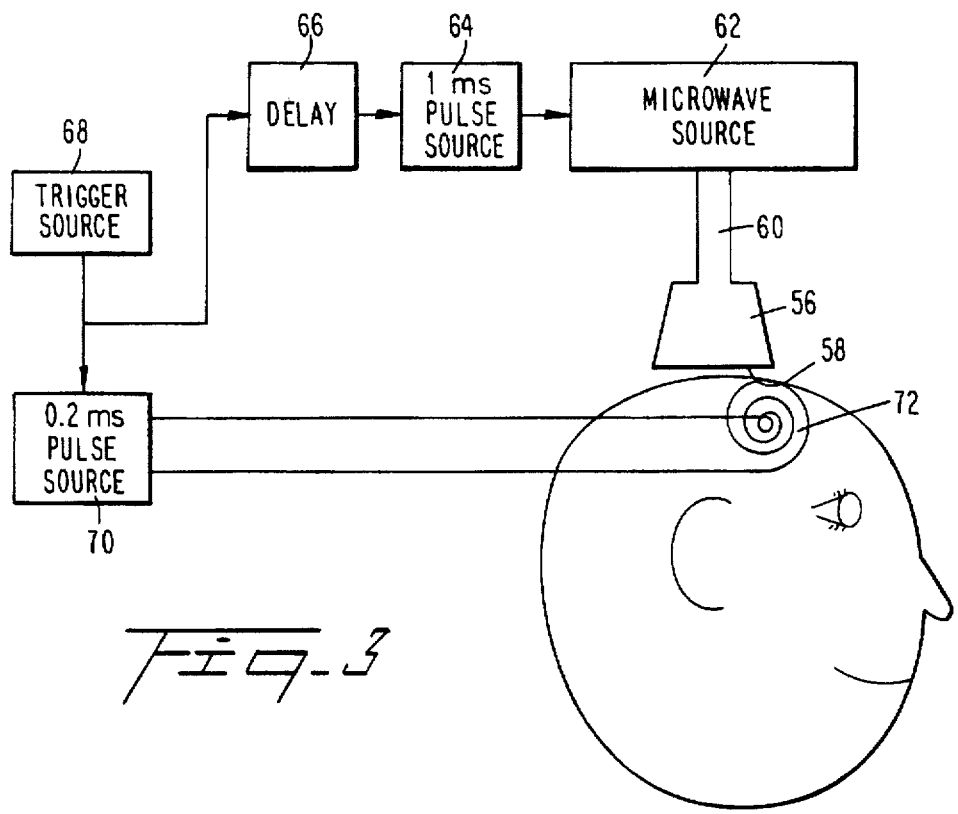
_Fig. 3_
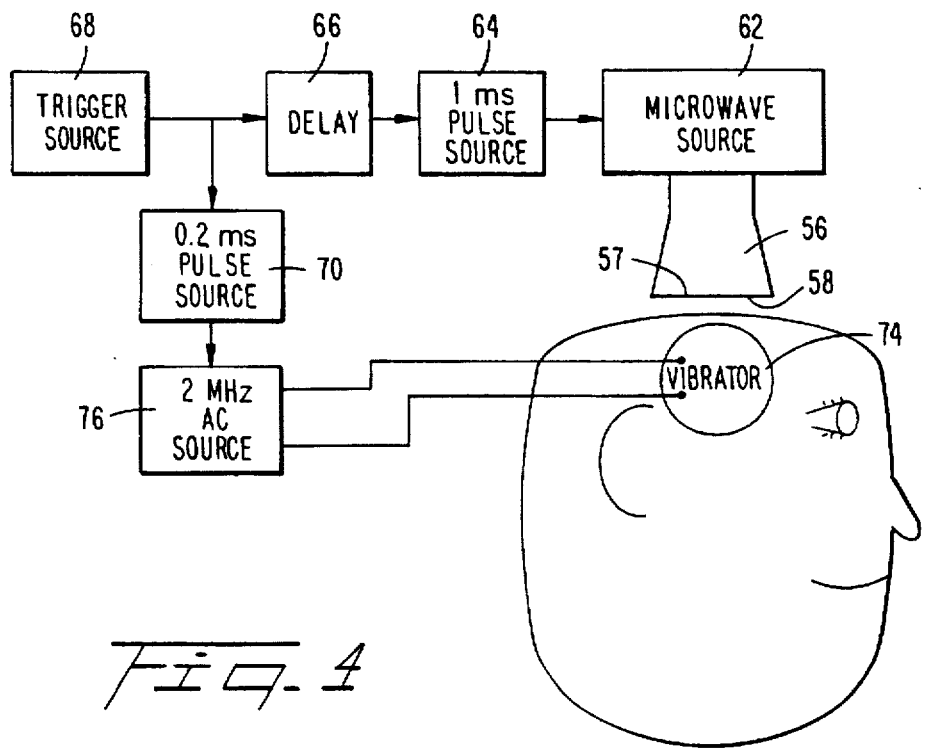
_Fig. 4_

METHOD OF AND APPARATUS FOR MAGNETICALLY STIMULATING NEURAL CELLS

RELATED TO EXISTING APPLICATION

The present application is a continuation-in-part application of U.S. patent application Ser. No. 08/074,507 filed Jun. 11, 1993, now abandoned.

FIELD OF INVENTION

The present invention relates generally to apparatus for and methods of magnetically stimulating neural cells, such as neurons and nerve cells, and more particularly to such an apparatus and method wherein effects of a conditioning energy field are combined with those of a cyclic magnetic component.

BACKGROUND ART

Magnetic stimulation is a clinically available technology recognized to be of value in a number of clinical settings, primarily because it provides non-invasive, painless and relatively safe semi-quantitative data concerning the location of motor system lesions. Nervous system magnetic stimulation has been clinically used to diagnose and evaluate multiple sclerosis, cervical spondylotic myelopathy and other degenerative and hereditary disorders of cortical white matter, spinal column white and gray matter and peripheral motor tracts. Other important applications include mapping cortical motor and speech areas to evaluate patients prior to epilepsy surgery and obtaining motor evoked potentials for intra-operative monitoring during brain and spine surgery. Nervous-system magnetic stimulation has also been used to assess motor system development, organization and recovery from injury.

Prior art nervous-system magnetic stimulation processes and devices have not achieved precise focusing during intracranial stimulation. The systems developed to the present time have limited stimulation to relatively large area cortical surfaces of at least 7 square centimeters. This limitation has prevented magnetic stimulation from being used to, differentiate extrapyramidal from pyramidal tract lesions on a neurophysiological basis; more precise localization of lesions within the cranium, including brain stem regions; neurophysiological investigations of limbic, diencephalic and brain stem areas; as well as brain-mapping, on a par currently attained by using subdurally-implanted electrodes arrayed on a 1×1 centimeter grid. Subdurally-implanted electrode arrays are disadvantageous because they are invasive, painful and relatively unsafe.

It is, accordingly, an object of the present invention to provide a new and improved apparatus for and method of supplying focused magnetic stimulation to neural cells.

An additional object of the invention is to provide a non-invasive, painless and relatively safe method of and apparatus for differentiating extrapyramidal from pyramidal tract lesions on a neurophysiological basis, to provide more precise location of motor tract and other lesions within the cranium, including brain stem regions and neurophysiological investigations of limbic, diencephalic and brain stem areas and brain-mapping capabilities.

As disclosed by Eaton, *Johns Hopkins APL Technical Digest*, Vol. 12, No. 2, (1991), pages 153–158 and in Chapters 3 and 4, pages 13–43 of the book *Magnetic Stimulation in Clinical Neurophysiology*, magnetic stimulators derive magnetic fields causing eddy currents to be generated in neural cell tissue. Eaton reports that a high-amplitude current pulse (e.g. about 5300A. peak) having a relatively short duration (e.g. 450 microsecond) applied to a stimulus coil induces a damped sinusoidal electric field (E-field) in the cell. Cohen et al., *Clinical Neurophysiology*, Vol. 8, No. 1 (1991) pages 102–120 indicates that magnetic stimulation focality can be improved by supplying a high amplitude pulse (e.g. 25,000A. peak) to a coil having a figure eight (8) configuration. A damped sinusoidal current can also stimulate a neurological cell, as reported by Caldwell in U.S. Pat. Nos. 4,940,453 and 5,047,005, as well as in Chapter 4 of the previously mentioned book. From the foregoing, the prior art requires very substantial currents to be supplied to an excitation coil, leading to possible breakdown problems, possible injury to the subject, and specialized sources.

It is accordingly another object of the present invention to provide a magnetic neural cell stimulator having reduced current requirements.

The mechanism involved in electrical stimulation of a myelinated neuron cell is discussed by Reilly in *Johns Hopkins APL Technical Digest*, Vol. 9, No. 1 (1988), pages 44–59. In a quiescent state, the voltage for mammals inside the cell is about −90 mv. relative to the voltage outside the cell; the potential across the cell membrane is referred to as the transmembrane potential. The rest state potential is due to different concentrations of ions (primarily $Na^+$ and $K^+$) on opposite sides of the membrane. The membrane can be modeled as parallel branches respectively including non-linear conductances $g_{Na}$ and $g_K$, each in series with opposite polarity potential sources $E_{Na}$ and $E_K$. In response to sufficient electric stimulation, there are quasi-step changes in the values of $g_{Na}$ and $g_K$ so the value of $g_{Na}$ goes from a value less than $g_K$ to a value in excess of $g_K$. The branches including $g_{Na}$ and $g_K$ are shunted by two additional branches, respectively including a capacitor and a linear conductance, $g_L$, in series with another DC potential source, $E_L$, having the same polarity as $E_K$. With sufficient electric stimulation, causing ion migration across the membrane, the quasi-step changes in $g_K$ and $g_{Na}$ occur, causing the cell transmembrane potential to change suddenly to +20 mv in mammals; the cell when "fired" to +20 mv, is in the depolarized state. There are intermediate transmembrane potentials between the polarized and depolarized states, referred to as hyperpolarized states.

The values of $g_{Na}$ and $g_K$ are determined by the transmembrane potential, in turn determined by the values of the conductances, capacitor and potentials. Because of the nonlinearity of $g_{Na}$ and $g_K$ and the effects of the shunt capacitor, the application of AC stimulation having an appropriate frequency causes an incremental transmembrane potential change during each cycle of the stimulation. The temporal effects of $g_{Na}$, $g_K$, $g_L$ and the membrane capacitance are referred to as the cell integration time constant.

To achieve some degree of temporal integration of a cyclic magnetic stimulus pattern, the stimulus sequencing time, i.e. a period of AC applied to the cell, must be a fraction of a temporal integration time constant of a nerve being stimulated. Temporal properties of nerve excitation are traditionally described in terms of a strength-duration (S-D) time constant. The strength-duration time constants have been determined experimentally for peripheral nerve stimulation to be in the range from about 50 microseconds to nearly 1 millisecond. The temporal integration period extends to several strength-duration time constants.

The strength-duration time constant is a property of the excitable tissue, as well as a distribution of current flux due to ion migration crossing the fatty, normally non-conductive neural membrane. The time constant diminishes as the membrane current flux distribution increases in density and increases as the current flux density decreases. Membrane current flux responds to both the spatial properties of the induced electric field and the shape of the cell. Two factors contributing to membrane current flux density are large values of induced electric field gradient and sharp bends in cell shape.

The stimulated region depends on the polarity of the stimulus, i.e., the direction of the induced electric field. A magnetically induced electric field is, of necessity, a charge-balanced stimulus having positive and negative phases.

THE INVENTION

In accordance with one aspect of the present invention, a method of stimulating a neural cell from a polarized quiescent state to an active, fired state having a transmembrane potential substantially different from the quiescent state transmembrane potential comprises applying a first energy field to the cell to change the cell from the quiescent state so the cell transmembrane potential differs from the quiescent and active states. While the transmembrane potential differs from the quiescent and active states, a field including a cyclic magnetic component is applied to the cell. The cyclic magnetic component has a frequency and amplitude and is combined with the effects of the first energy field such that each cycle of the cyclic magnetic component causes an incremental change in transmembrane potential of the cell without changing the cell between the quiescent and active states. The cyclic magnetic component applied to the cell has a duration and amplitude and is combined with the effects from the first energy field to cause an accumulation of the incremental transmembrane cell potentials to change the cell from the quiescent to active state. Thereby, the cell is transferred between states without supplying a relatively large current to a coil which derives the magnetic field component.

In accordance with another aspect of the invention, an apparatus for performing the previously indicated neural cell stimulating method comprises a first means for applying the first energy field to the cell and second means synchronized with the first means for applying a field including the cyclic magnetic component to the cell while the transmembrane potential differs from the quiescent and active states.

In certain embodiments of the invention, the first energy field is derived by supplying a unipolar constant pulse to a first coil while a second coil is excited by AC current having a period less than the strength duration time constant. The second coil preferably produces an asymmetrical magnetic field, a result which can be achieved by vibrating the second coil in synchronism with the application of current to the coil.

In another embodiment, a volume including, but considerably in excess of, the volume where the cells to be stimulated are located, is hyperpolarized by applying DC unipolar current pulses to coils enclosing the volume. A depolarizing field is applied via another coil to the cells to be stimulated while remaining cells in the volume are hyperpolarized.

In still further embodiments of the invention, the cyclic magnetic component is derived from a microwave source and the first energy field can be derived from various sources, such as by supplying a unipolar current pulse to a coil or from a focused ultrasonic compressional wave.

The cyclic magnetic component is, in certain embodiments, asymmetrically coupled to the cell so the magnetic component coupled to the cell has greater amplitude during one half cycle of the component than during a second half cycle of the component. To this end, the magnetic coil for deriving the magnetic component may be vibrated in synchronism with the application of AC current to the magnetic coil.

According to another aspect of the invention, the method is performed by placing plural magnetic coils proximate different locations of a subject, including the neural cell to be stimulated. The different coils are energized with currents having differing temporal characteristics so the current applied to one of the coils includes a cyclic component. Magnetic fields resulting from the currents energizing the different coils are coupled to the cell so the magnetic field from at least one other of the coils causes the cell transmembrane potential to change from a quiescent state to a state between the quiescent state and an active, fired state. The cyclic component is applied to the cell while the transmembrane potential differs from both the quiescent and active states. The cyclic magnetic component has a frequency and amplitude and is combined with effects from the magnetic field from the other coil such that each cycle of the cyclic magnetic component causes an incremental change in transmembrane potential of the cell without changing the cell from the quiescent to the active state. The cyclic magnetic component applied to the cell has a duration and amplitude and is combined with the effects of the magnetic field from the other coil to cause an accumulation of the incremental changes to change the cell state from the quiescent to the active state.

The above and still further objects, features and advantages of the present invention will become apparent upon consideration of the following detailed descriptions of specific embodiments thereof, especially when taken in conjunction with the accompanying drawings.

BRIEF DESCRIPTION OF THE DRAWING

FIG. 3 is a schematic diagram of another embodiment of the invention employing a unipolar magnetic field in combination with a microwave field for stimulating neuron cells;

FIG. 4 is a schematic diagram of still another embodiment of the invention wherein a microwave field is combined with a focused ultrasonic, compressional wave field for stimulating neuron cells;

BEST MODES FOR CARRYING OUT THE INVENTION

Figure 1:
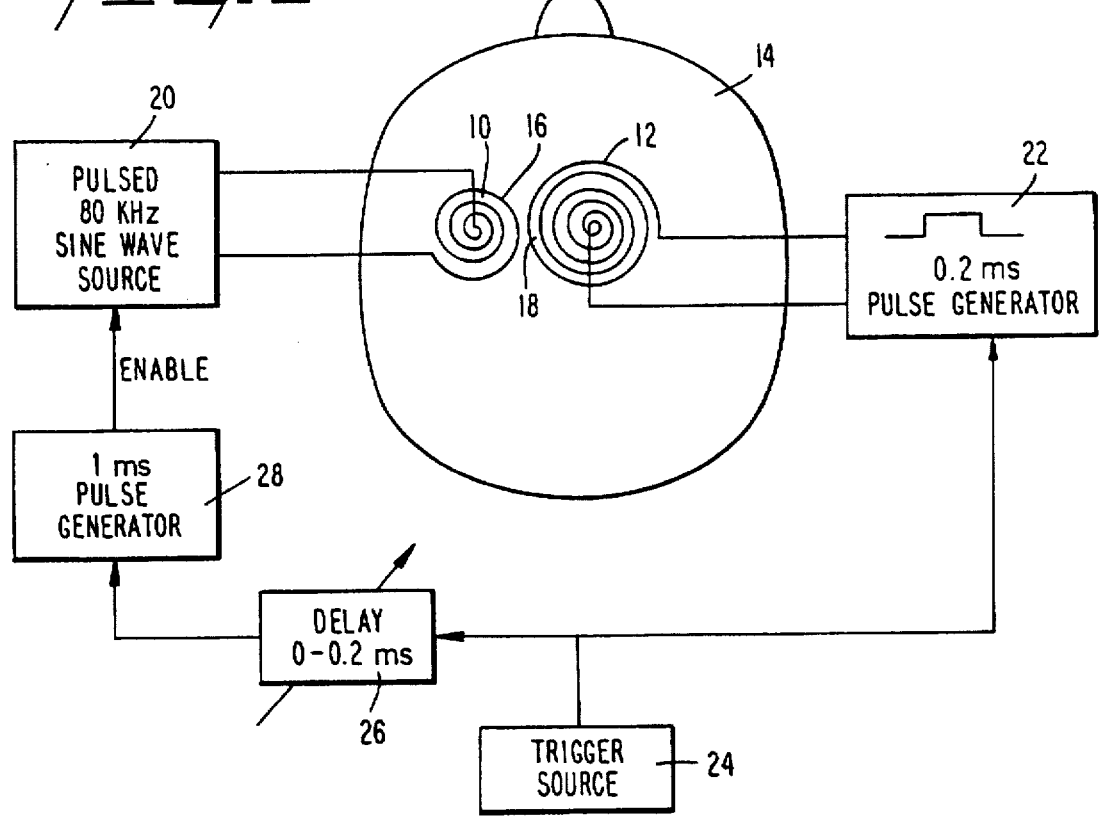
FIG. 1 is a schematic diagram of one embodiment of the invention employing first and second coils respectively driven by bipolar and unipolar excitation currents.

Reference is now made to FIG. 1 of the drawing, a schematic view of one embodiment incorporating the present invention for stimulating neuron cells in the brain of a human individual. Two, side-by-side flat, pancake type spiral coils 10 and 12 are placed on head 14 of a human subject. The neuron cells to be stimulated are located along a line beneath adjacent outer regions 16 and 18 of coils 10 and 12, respectively. In one embodiment, each of coils 10 and 12 includes the same number of turns, for example, 10, with coil 10 having a diameter somewhat less than half of the diameter of coil 12; in the stated embodiment, coils 10 and 12 respectively have diameters of 2.5 and 6 centimeters. The turns of coils 10 and 12 are arranged so the magnetic fluxes derived from the coils additively combine with maximum amplitude along the previously mentioned line in the neuron cells to be stimulated in head 14 to provide focused stimulation within the brain.

End terminals of coils 10 and 12 are respectively connected to pulsed sinusoidal (bipolar) source 20 and ramped (unipolar) pulse source 22 having a waveshape somewhat similar to the trapezoidal waveshape applied to a television cathode ray tube deflection coil. In one preferred embodiment, source 20 derives an 80 kHz sinusoidal, carrier like wave for a duration of 1 millisecond while a positive going ramp is derived from source 22 for 0.2 milliseconds, after which the current of source 22 is maintained constant for about 0.2 milliseconds or decreases gradually. -For different frequencies of source 20, there are corresponding proportional changes in the voltage induced in the neurons induced by the field from source 20. Other suitable frequencies, as low as 10 kHz, can be derived from source 20 and the on-time of the source can be other suitable values; the duration and shape of the pulse from source 22 can be changed as necessary.

To enable the waves from sources 20 and 22 to be supplied either sequentially or simultaneously to coils 10 and 12, operation of the sources is synchronized by trigger source 24, having an output supplied in parallel to pulse source 22 and variable delay circuit 26. Pulse source 22 responds to the output of trigger source 24 to derive the 0.2 millisecond quasi-square wave unipolar pulse that is applied to coil 12, while delay circuit 26 delays the output of trigger source 24 between 0 and 0.2 milliseconds. Pulse generator 28 is connected to respond to the output of delay circuit 26 to derive a quasisquare wave having a duration of 1 millisecond that is supplied to an enable input of source 20. Thereby, 80 cycles of sinusoidal current are supplied to coil 10 by source 20 for 1 millisecond.

Coils 10 and 12 respond to the currents supplied to them to derive magnetic fluxes which are coupled to target neurons to be stimulated; coil 10 responds to the AC current supplied to it to derive an AC magnetic field while coil 12 responds to the ramp current supplied to it to derive a relatively constant DC magnetic field during the ramp. Thereafter, the DC magnetic field suddenly decreases. The flux from coil 10 or 12 by itself is insufficient to stimulate the target neurons from the polarized quiescent state to the depolarized, active or fired state. The effects of the magnetic fluxes are additively combined in the target neuron cells to cause the cells to be transferred from the quiescent state to the active, fired state. The magnetic field from coil 12 causes the transmembrane potential of the target neurons to be raised from the quiescent state to an intermediate state having a transmembrane potential which is somewhat less than the active, fired state; e.g. the transmembrane potential is raised to about 90% of the difference between the polarized and depolarized potentials of the target neurons. Because the neuron to be stimulated (target neuron) has non-linear memory properties, the effects of the DC magnetic field persist in the target neuron and are combined with the effects of the AC magnetic field even after the DC magnetic field has a negligible effective value.

Coil 10 produces a cyclic magnetic field component having a frequency and amplitude such that each cycle of the magnetic component (hence of source 20) causes an incremental change in transmembrane potential of the target neuron cells without changing the cells from the quiescent to the active state. The duration and amplitude of the cyclic magnetic component applied to the target neuron cells by coil 10 (hence the amplitude and on time of source 20), combined with the effects of the magnetic field from coil 12, result in an accumulation of the cell incremental changes so the target cells are changed from the quiescent to the active state, i.e., to cause the cells to be fired or stimulated.

In effect, the magnetic field from coil 12 produces a sub-threshold "conditioning" stimulus which makes the target cell tissue more excitable and greatly reduces the current requirements of coils 10 and 12. The interaction of the magnetic fields from coils 10 and 12 takes advantages of non-linear neuron properties, which have been studied using a myelinated nerve model incorporating a Frankenhaeuser-Huxley non-linear membrane electrodynamic equation. This equation is based on the fact that the neuron has an intracellular high concentration of potassium ($K^+$) ions and an extracellular high concentration of sodium ($Na^+$) ions. The neuron includes a membrane made of fat, is electrically non-conductive and includes channels that change from a closed to an open state as the cell changes from the quiescent to the active state. In response to electrical stimulation resulting from the magnetic fields, sodium ions enter one region of the cell membrane and are replaced with ions from another region. The ion transfer is sequential and occurs in response to current that is induced in the cells by the magnetic fields. As the threshold to reach the active state is approached, almost all of the channels open to thereby form a non-linear type of circuit response. The channels are thus considered as "voltage gated sodium channels." Sodium ions move into the cells, creating a small current which propagates along the cell membranes. When all of the channels open, a voltage change occurs, associated with cell firing.

The interaction efficiency between the magnetic fields from coils 10 and 12 depends on various parameters, including the magnitude of the current supplied to the coils, the timing of the waveforms applied to coils 10 and 12 and the frequency of the current applied to coil 10. Consider the situation of coil 12 supplying a 0.2 millisecond conditioning E-field having an amplitude to achieve 90% of the firing threshold of the target neurons and a sinusoidal waveform having an 80 kHz frequency being applied to coil 10 for 1 millisecond. It has been shown that if coils 10 and 12 are sequentially excited with these parameters such that the field from coil 10 starts immediately after the field from coil 12 has terminated, the amplitude of the current applied to coil 10 for stimulation of the target neuron cells must be 50% of the amplitude of the current supplied to coil 10 if only coil 10 were used for stimulation. In contrast, if the waveforms applied to coils 10 and 12 have simultaneous leading edges, the amplitude of the current supplied to coil 10 to achieve stimulation is only 29% of the current which must be applied to coil 10 without the presence of the magnetic field from coil 12.

It has also been found that the apparatus illustrated in FIG. 1 has considerably improved focality compared to the prior art device disclosed by Cohen et al. (supra) wherein two symmetric flat, spiral pancake loops of a single coil are connected in series with each other. Improved focality is attained with the present invention because of the small size of coil 10 compared to the prior art, providing a smaller region of peak magnetic flux density. If such a small coil were excited according to the prior art, a prohibitively large current would be needed to enable the small peak flux density in the correspondingly small cross sectional area to penetrate the skull and reach the brain. In contrast, the combined effects of the magnetic fields from coils 10 and 12 enable the peak currents needed relative to a single coil situation employing two series connected loops to be reduced significantly.

Figure 2:
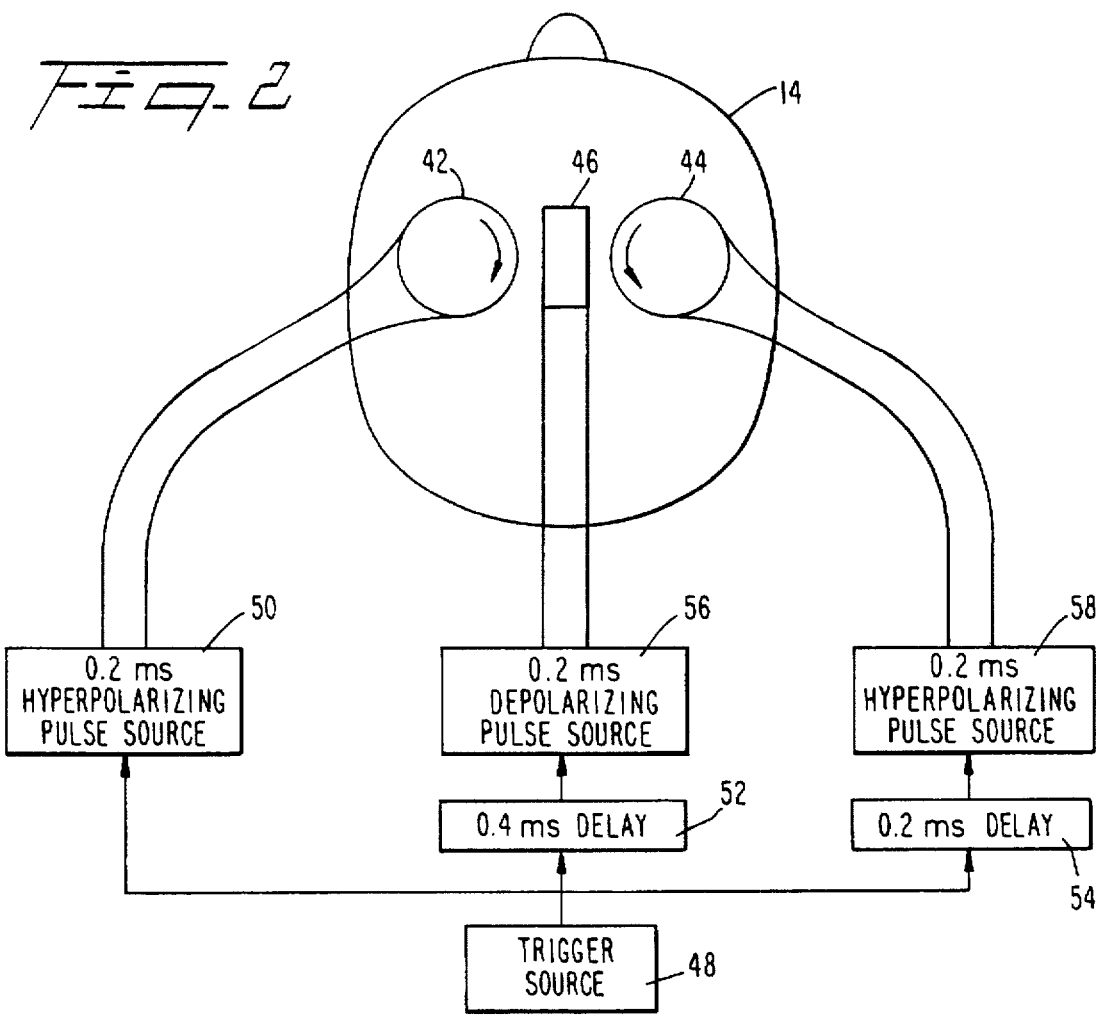
FIGS. 2 and 2a are respectively top and side views of another embodiment of the invention wherein hyperpolarizing unipolar magnetic fields and a depolarizing unipolar magnetic field are applied to the cells.
Figure 2A:
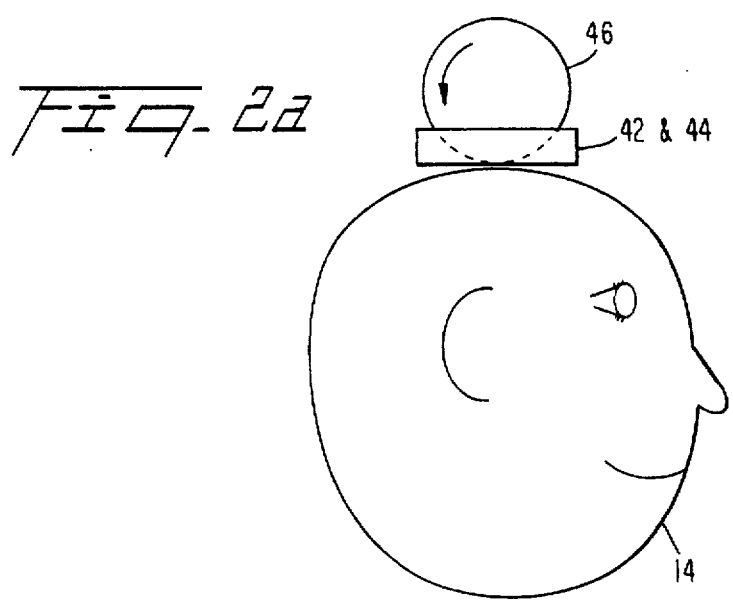

A further embodiment of the invention is illustrated in FIGS. 2 and 2a wherein flat, spiral pancake coils 42, 44 and 46 are located on head 14 of a subject, such that coils 42 and 44 are placed on and towards opposite sides of the head and brain, while coil 46 is placed standing on edge on the head and above the brain and target neuron cells.

Coils 42 and 44 simultaneously supply magnetic fields to a large volume of the brain of the subject to hyperpolarize the neuron cells therein, i.e., the transmembrane potential of the neuron cells in the volume is increased to a more negative level than the polarized, quiescent state. A depolarizing field is applied by coil 46 to the target neurons desired to be stimulated while the neuron cells to the sides of the target region have been hyperpolarized and rendered incapable of being stimulated by a stimulating impulse of the magnitude supplied by coil 46. Any one of bipolar, unipolar or ramping currents is supplied to coils 42, 44 and 46. The pulses of coils 42 and 44 have a duration less than, the same as, or greater than the on-time of the current supplied to coil 46.

To these ends, for the embodiment of FIGS. 2 and 2a, trigger source 48 supplies trigger pulses in parallel to ramping wave pulse source 50 and delay elements 52 and 54. Pulse source 50 responds to the trigger pulse supplied to it to derive a 0.2 millisecond unipolar ramped current pulse that is supplied to coil 42. Delay circuit 54, after imposing a delay time of approximately 0.2 milliseconds on the trigger output of source 48, activates pulse generator 58 into an active state, causing a 0.2 millisecond unipolar ramped current pulse to be applied to coil 44. In addition, delay circuit 52, after imposing a delay time of approximately 0.4 milliseconds on the trigger output of source 48, activates pulse generator 56 into an active state, causing a 0.2 millisecond unipolar ramped current pulse to be applied to coil 46.

Thus, unipolar magnetic fluxes each having a duration of 0.2 milliseconds are thereby supplied by coils 42 and 44 to an extensive region of the brain of the subject, to hyperpolarize the neurons in this region. After the neurons in this region have been hyperpolarized by the fluxes from coils 42 and 44, depolarizing current is supplied by ramping source 56 to coil 46 for 0.2 milliseconds.

The magnetic fields from coils 42 and 44 act to hyperpolarize subjacent neurons more than they act to hyperpolarize the neurons subjacent to coil 46; hence, the transmembrane potential of these cells is increased to a more negative level than the quiescent state. The magnetic field from coil 46 is focused on the target cells to depolarize these cells. The size of the target region is effectively decreased by the adjacent zones of hyperpolarized neurons which cannot be sufficiently depolarized by the magnetic field from coil 46 to change them from the quiescent to the active state.

This technique for delimiting the effective size of the target region by using adjacent hyperpolarizing coils can be combined with any of the other embodiments of the invention to further fine tune the size of the stimulated region. Furthermore, numerous combinations of unipolar, bipolar and ramping pulse patterns can be used to achieve the desired end.

Another embodiment of the present invention is illustrated in FIG. 3 as including microwave field excitation, in combination with unipolar or AC magnetic field excitation of target neuron cells. Microwaves are coupled to the target neurons by microwave horn 56, having an aperture 58 immediately above the neurons to be treated. Horn 56 is connected to one end of wave guide 60, having a second end connected to pulsed microwave source 62, having a frequency such as 2.8 gigahertz.

Microwave source 62 is enabled by the output of pulse source 64, in turn responsive to the output of delay circuit 66, driven by trigger source 68. The output of trigger source 68 also drives pulse source 70 in parallel with delay circuit 66. Pulse source 70 responds to a pulse from trigger source 68 to derive a unipolar or AC pulse having a predetermined duration, such as 0.2 millisecond. The pulse from source 70 can also be ramped as described for source 22. The output of source 70 is applied to flat pancake, spiral coil 72, constructed the same as coil 12, FIG. 1. Delay element 66 has a variable delay, such as between 0 and 0.2 milliseconds, so microwave energy is supplied by horn 56 to the target neurons simultaneously or sequentially with the application of magnetic flux from coil 72.

The magnetic field from coil 72 conditions the neurons to be stimulated in the same manner that the magnetic field from coil 12 stimulates target neurons in the embodiment of FIG. 1. Tissue interactions with the microwave field from horn 56 are combined with the effects of the magnetic field from coil 72 to stimulate the target neurons in a manner similar to that described supra with regard to FIG. 1. Hence, the field derived from horn 56 interacts with the magnetic field from coil 72 in a similar manner to the way the magnetic field from coil 10 interacts with the magnetic field from coil 12.

The conditioning effects of coils 12 and 72 can be derived from other energy sources, such as from an ultrasonic high frequency source or an x-ray source that irradiates the target neurons. In FIG. 4 is illustrated an embodiment of the invention where a focused ultrasonic compressional wave source is used in combination with a microwave source. Ultrasonic transducer 74 is placed on top of the head in immediate proximity to side wall 57 forming aperture 58 of horn 56. Transducer 74 is excited by AC source 76, having a frequency such as 2 mHz, to produce a focused ultrasonic beam for irradiating the target neuron cells. It is believed the focused ultrasonic beam mechanically oscillates the target neurons to heat them, thereby lowering the current necessary to change the target cells from the polarized quiescent state to the active, fired state. The tissue interaction in response to the energy from horn 58 causes incremental changes in the transmembrane potential of the target neurons without changing these neuron cells to the fired state. The microwave energy from horn 56 is supplied for a sufficient length of time to cause accumulation of the incremental changes so the target neurons eventually change from the quiescent to the active state. If an x-ray source is used instead of the ultrasonic source, a similar mechanism is believed to occur in response to energy from the x-rays irradiating the target neurons.

Figure 5:
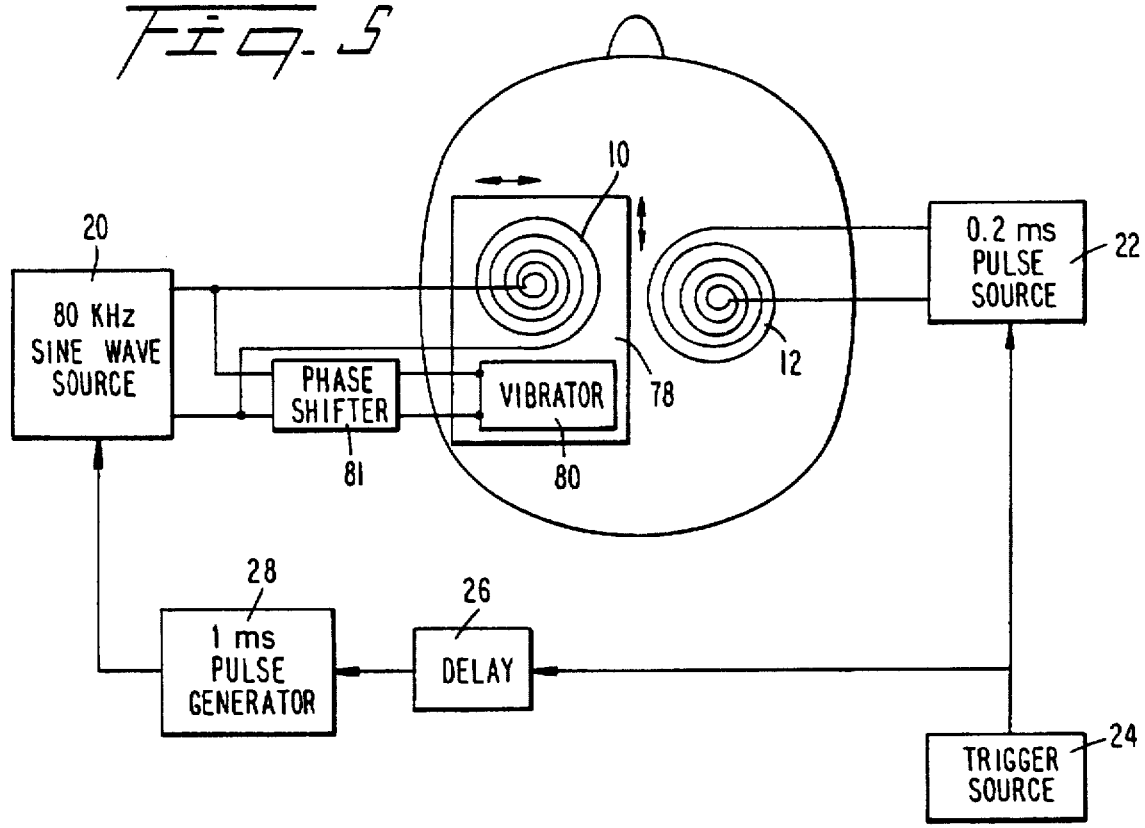
FIG. 5 is a schematic diagram of another embodiment of the invention wherein the apparatus illustrated in FIG. 1 is modified to supply an asymmetrical bipolar magnetic field to the stimulated cells by a coil carried on an ultrasonic vibrator.

In a further embodiment of the invention, illustrated in FIG. 5, the magnetic field derived from coil 10, FIG. 1 is asymmetrical so the magnetic field coupled to the target neurons resulting from the positive half cycles of the current flowing through the coil is greater than the magnetic field resulting from the negative half cycles. To this end, coil 10 is mounted on the lower face of ultrasonic vibrator 78, made of nonmagnetic material so it does not affect the magnetic field from coil 10. Vibrator 78 can be fabricated so it vibrates generally transversely of the top of head 14 of the subject, i.e., in a plane transverse to the plane of spiral, pancake winding 10. Alternatively, vibrator 78 can be arranged so it vibrates in approximately the same plane as coil 10.

Vibrator 78 includes excitation terminals 80, connected to variable phase shifter 81, which is driven in parallel with coil 10 by the output of pulsed sine wave source 20. Phase shifter 81 is adjusted so vibrator 78 and coil 10 physically vibrate in synchronism with the AC current flowing in the coil. The phases of the mechanical vibration of vibrator 78 and of the excitation current supplied to coil 10 are such that as the current flowing in the coil is undergoing a positive half cycle, the coil is in closest proximity to the top of the head of the subject, assuming transverse vibration of vibrator 78. Conversely, during negative half cycles of the current flowing in coil 10, the coil is moved transversely by vibrator 78 slightly away from the top of the head of the subject. Thereby, the AC magnetic field coupled from coil 10 to target neurons of the subject have a greater amplitude during positive half cycles than during negative half cycles. There is thereby applied an asymmetrical magnetic field to the neurons being stimulated, to cause greater incremental changes in the transmembrane potential of the neurons being stimulated during each cycle of source 20 than is attained with the structure of FIG. 1.

If vibrator 78 is arranged so it vibrates in the plane of coil 10, phase shifter 81 is adjusted so the peripheral edge of coil 10 in closest proximity to coil 12 is closest to coil 12 while positive current is flowing in coil 10. During negative half cycles of current flow through coil 10, vibrator 78 is energized so coil 10 is moved away from the proximal edge of coil 12. Thereby, greater magnetic flux is supplied to the target neurons during positive half cycles of current flowing through coil 10 than during negative half cycles. This asymmetry results in greater incremental changes in the transmembrane potential of the target neurons during each cycle of the AC current from source 20.

In another embodiment, compressional waves from an ultrasonic vibrator are focused at the tissues under the magnetic coil so to mechanically vibrate these tissues into and out of the magnetic field in synchronism with the positive and negative phases of the magnetic fields resulting from the AC current flowing in the magnetic coil. The target neurons are brought into the most intense field during the positive phase while other nearby non-target neurons are brought into the most intense field during the negative phase.

In another embodiment, several coils of varying but specific sizes responsive to bipolar or unipolar pulses of different specific amplitudes, durations, and frequencies are placed at different specific sites, about, above and below the head. The coils are excited with currents having different specific phase patterns and waveforms so the electric field induced in the target neurons by all the coils acting simultaneously and/or sequentially are incrementally increased toward depolarization. The incremental increases in depolarization are greater for the target neurons than the increases experienced by any other neurons in the head. Therefore, only the target neurons change from the quiescent to the active fired state. With this arrangement, the target neurons can be at any location in the brain, both on the surface and in the interior thereof.

Figure 6:
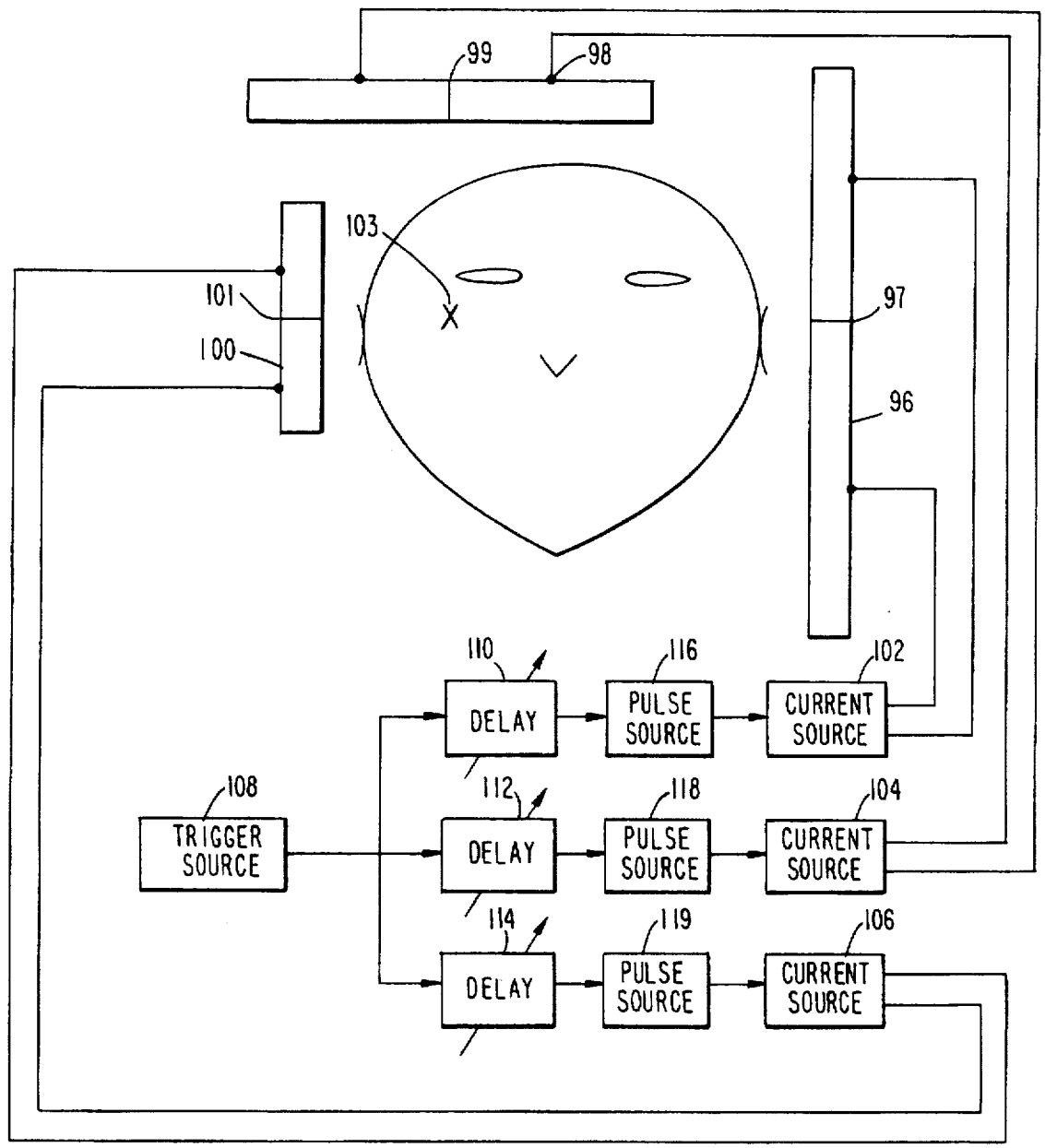
FIG. 6 is a schematic diagram of another embodiment including three different figure-eight shaped coils energized by different sources for differing times and located adjacent different portions of the head.

Consideration is now given to a specific arrangement of the aforementioned type by referring to FIG. 6 of the drawing wherein flat pancake coils 96, 98 and 100, each configured as a figure eight and including two series connected spiral coil segments, are placed on or adjacent the head of the subject. The smallest diameter coil 100 is located adjacent the left side of the head (as viewed in FIG. 6) while intermediate and largest diameter coils 98 and 96 are respectively located adjacent the top and right sides of the head. The planes of coils 96 and 100 extend vertically, generally parallel to the sides of the head, while the plane of coil 98 extends horizontally, generally parallel to the top of the head. Each of coils 96, 98 and 100 is arranged in a well-known manner so the magnetic fields from the two segments thereof are additive along a line extending through the junction of the two spiral halves of the coil at the coil center and at a right angle to the plane of the coil. Center junctions 97 and 101 of coils 96 and 100 are vertically aligned; target neurons are at region 103 at the intersection of lines extending through center junctions 97, 99 and 101 at right angles to the planes of coils 96, 98 and 100.

Coils 96, 98 and 100 are energized and de-energized in controlled sequences for different intervals and supplied by a network including current sources 102, 104 and 106 with AC or unipolar cyclic currents that may have different amplitudes. Sources 102, 104 and 106 have the same frequency and are synchronized with each other and derive currents having asymmetrical characteristics such that the slope of the positive going portion of each cycle is greater than (preferably twice) the slope of the negative going portion of each cycle. Thereby, the resulting magnetic field derived from each coil during the positive going portion of each current cycle is greater than the resulting magnetic field derived from that coil during the negative going portion of each current cycle. The effects of the greater magnetic fields during the positive going portion of each current cycle are accumulated by the non-linear memory characteristics of the neurons responsive to the magnetic fields. The currents flowing in coils 96, 98 and 100 are phased so the current supplied to intermediate coil 98 has a minimum value (either zero for a unipolar current or maximum negative for AC) when the current supplied to smallest coil 100 has a positive peak value. The current supplied to largest coil 96 has a minimum value when the current supplied to intermediate coil 98 has a positive value and when the current in coil 100 has a value halfway between its peak positive and lowest values, assuming that each current has a positive going slope twice that of the negative going slope. This preferred phase relation enables the magnetic field from largest coil 96 to at least partially counterbalance the effects of the magnetic fields from coils 98 and 100 which tend to return the target cells toward the quiescent state.

To achieve these results, sources 102, 104 and 106 are synchronized in response to pulses derived by trigger source 108 which drives variable delay circuits 110, 112 and 114 in parallel. Output pulses of circuits 110, 112 and 114 respectively control when pulse sources 116, 118 and 119 are activated. Pulse sources 116, 118 and 119 derive pulses that may have different widths for respectively enabling current sources 102, 104 and 106 to supply currents having appropriate phases and durations to coils 96, 98 and 100. Because of the non-linear memory effects of neurons, current sources 102, 104 and 106 can be energized in sequence by pulse sources 116, 118 and 119.

Figure 7:
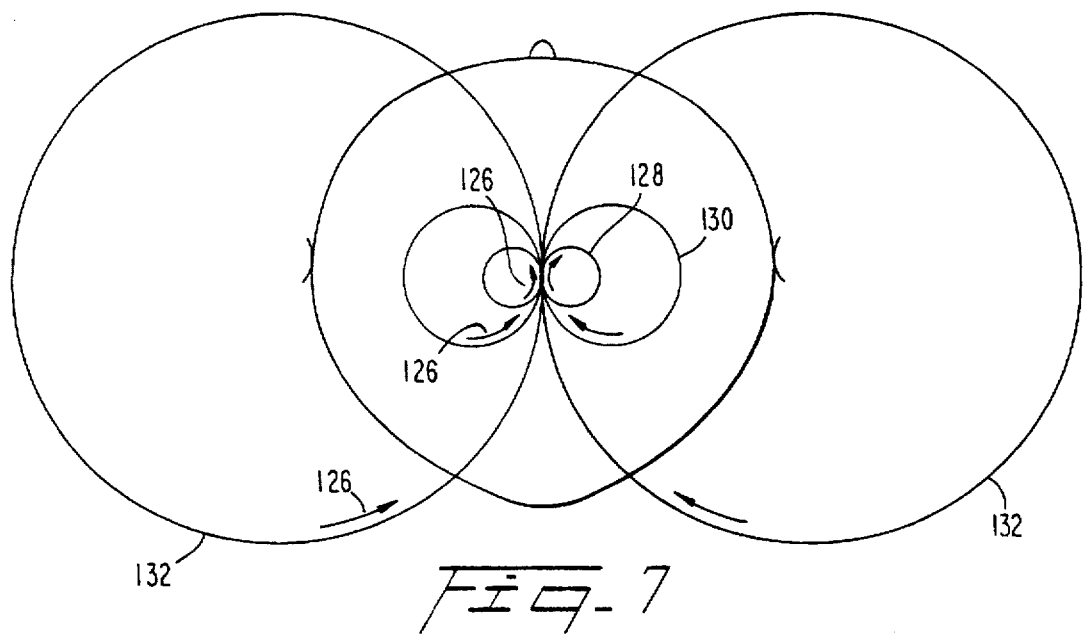
FIGS. 7 and 8 are respectively top and side views of a further embodiment including three sandwiched figure-eight shaped coils having a common axis.
Figure 8:
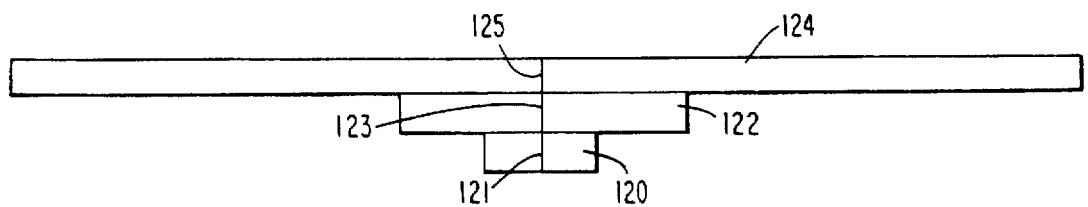

In the embodiment of FIGS. 7 and 8, pancake coils 120, 122 and 124 lie in mutually parallel planes above the head of the subject and are arranged so center junctions 121, 123 and 125 thereof lie on a line extending through the target neurons. The smallest diameter coil 120 abuts the head of the subject, while intermediate diameter coil 122 is sandwiched between largest diameter coil 124 and coil 120. Coils 120, 122 and 124 are energized and de-energized in controlled sequences for different intervals and supplied with AC or unipolar cyclic currents having different amplitudes and preferably asymmetric phases by a network of the type illustrated in FIG. 6.

All double-sided series-connected spiral pancake coils (referred to as "figure-eight" coils) are oriented and energized such that unipolar or bipolar current flows in the same direction in wires at the junction regions of the two sides of the said figure-eight coils.

The magnetic field produced by the current in the wires of coils 120, 122 and 124 is referred to herein as acting to depolarize the subjacent neurons when the current has a positive slope.

In one embodiment, each spiral side of coil 120 has a diameter of, e.g., 2 cm., and a specific current waveform is applied to it. The waveform has a specified frequency (e.g., 80 kHz), peak amplitude (e.g., 1600A) and duration (e.g., 800 microsecond). Current flows in intermediate-sized double spiral series coil 122 in the same direction in wires on both sides of junction region 123 in a direction to cause neuron depolarization. The direction of current flow in coil 122 depends on the specific orientation of the subjacent neurons to be activated.

The current begins to flow in coil 122 at a specified time (e.g., it begins at the onset of current flow in coil 120) for a specified duration (e.g., 800 microseconds) and has a specified peak amplitude (e.g., 2800A). The current in coil 122 may be shaped so it remains at a specified peak amplitude for a prolonged interval which is the best condition for activating cells; to avoid heating problems, the current in coil 122 first increases to its peak amplitude in the positive sloping direction for 200 microseconds and then reverses for a duration of 200 microseconds until the current minimum value is reached. The current then increases again to its maximum positive value for 200 microseconds. After reaching the maximum peak value, the current decreases for 400 microseconds until it reaches its minimum value. Thereby, hyperpolarizing forces at the target neurons are minimized.

Each spiral half of coil 122, typically has a diameter of about 6 cm.

The current in largest coil 124 which has a specified diameter and number of turns (e.g., 30 cm on each side of the double spiral and ten turns) flows similarly at junction 125 to the current flow in intermediate-sized coil 122. The current in coil 124 causes a depolarizing effect in the target neurons when the current has a positive slope. Furthermore, the current in coil 124 has specified frequency, duration, peak amplitude, waveshape and relative time characteristics; e.g., the onset of current flow in coil 124 occurs 200 microseconds after the onset of current flow in smallest coil 120.

In the embodiment of FIGS. 7 and 8, the current in largest coil 124 rises in a direction to cause neuron depolarization and has a magnitude sufficient to offset the hyperpolarizing effect in the neurons of the downward sloping (in this example) current of both the smallest and intermediate coils 120 and 122. In FIG. 7, the depolarizing effects of coils 120, 122 and 124 on the target neurons are provided by magnetic fields having directions and locations respectively indicated by arrows 126 and by lines 128, 130 and 132. At the time the current in the smallest coil 120 is flowing in the direction to cause neuron depolarization, the current in the largest coil 124 only needs to offset the hyperpolarizing tendency of the current in intermediate coil 122. Thus, the rate at which the current in coil 124 increases while the currents in coils 120 and 122 are flowing in opposite directions is less than the rate when the currents in both small coil 120 and intermediate coil 122 are flowing in directions tending to cause hyperpolarization.

It is to be emphasized that the current flowing in coil 124 could be less than, equal to, or greater than that required to completely offset the hyperpolarizing effect of coils 120 and 122 and that the specifications given herein are merely exemplary of possible current waveforms. Also, the sizes, shapes and orientation of all the coils can be varied in any desired fashion, e.g., as illustrated in FIG. 6.

After the positive going portion of the current flowing in largest coil 124 is complete, the current in coil 124 could (1) remain the same, (2) decrease slowly, with a smaller slope than the negative slope in either of coils 120 or 122, or (3) increase at some other specified rate. In one particular embodiment, the current in largest coil 124 decreases in 200 microseconds from its peak positive amplitude to a value half-way between its peak positive amplitude and lowest value (peak negative or zero or minimum positive) and increases from its lowest value to ¾ its peak amplitude in 200 microseconds. Because coil 124 has a much larger diameter than either of coils 120 or 122, coil 124 is able to withstand much larger currents than either of coils 120 or 122 and can absorb the attendant forces tending to disrupt the integrity of the coil component materials. The current in largest coil 124 is limited by heating considerations and the effects thereof on the subject.

Figure 9:
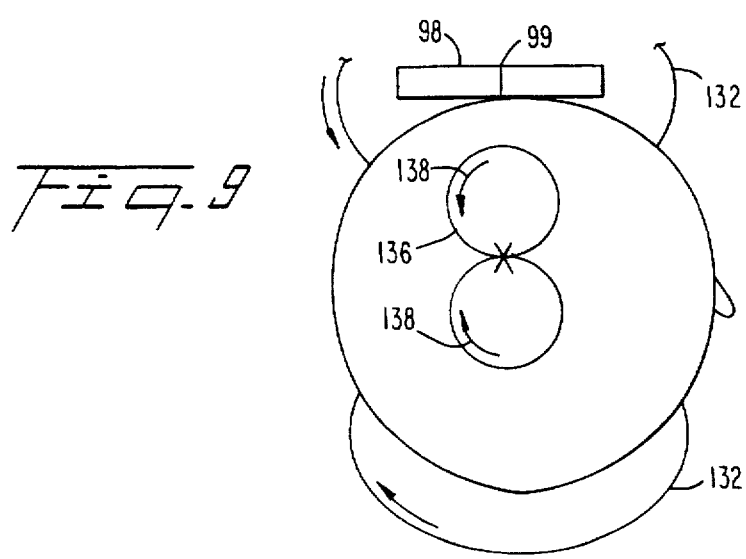
FIG. 9-11 are respectively magnetic coils on the left and right sides of the head (as viewed in FIG. 6) and the top of the head resulting from the apparatus of FIG. 6.
Figure 11:
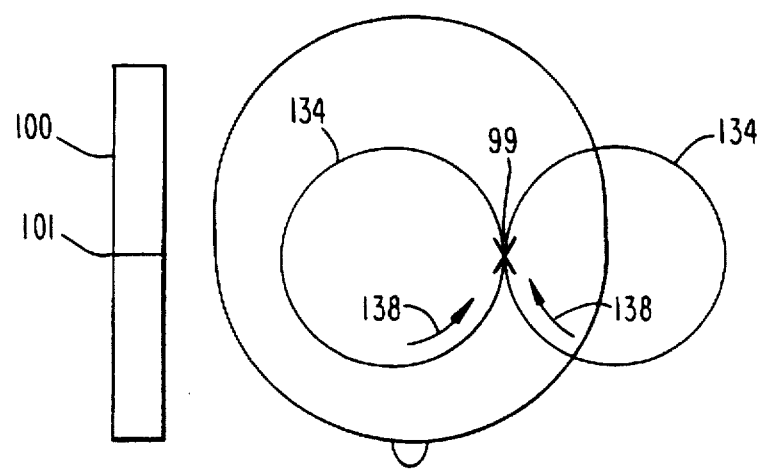
Figure 10:
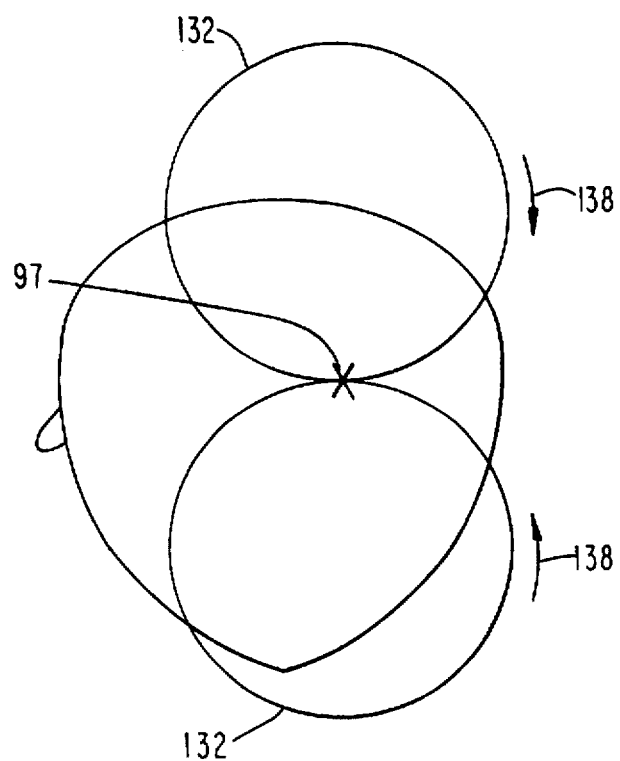

Coils 96, 98 and 100 (FIG. 6) produce magnetic fields as illustrated by lines 132, 134 and 136 in FIGS. 9–11, respectively. When coils 96, 98 and 100 are supplied with currents that produce magnetic fields causing neuron depolarization, the field directions are indicated by arrows 138. The magnetic fields are sequenced, phased and located to provide effects leading to neuron depolarization in region 103 during each cycle of the composite current waveforms applied to coils 96, 98 and 100. The depolarization effects are accumulated over many cycles of these waveforms until the neurons are stimulated, without stimulating adjacent neurons. A similar depolarization accumulating mechanism occurs in the embodiment of FIGS. 7 and 8 on neurons along the common axis of coils 120, 122 and 124 in response to the cyclic currents flowing in these coils.

While there have been described and illustrated specific embodiments of the invention, it will be clear that variations in the details of the embodiments specifically illustrated and described may be made without departing from the true spirit and scope of the invention as defined in the appended claims.

In all embodiments utilizing microwave or ultrasonic energy directed at the tissues, a phased array could be employed to achieve selective focus in the interior or on the surface of the brain.

In other embodiments, a single coil energized by an AC pulse could be used to incrementally fire the cells.

In another embodiment, ultrasonic energy is utilized so target neurons in the interior of the brain, lying under the magnetic coil, are alternately mechanically compressed and expanded with attendant increases and decreases in electrical conductivity. This activity is timed in such a way that the target neurons and a pathway leading to them from the brain surface are respectively compressed and expanded during positive and negative phases of the magnetic field fluctuations. By creating a preferred pathway of electrical conduction from the brain surface, the ultrasound facilitates stimulation in the brain interior under conditions that would otherwise lead to stimulation only at the brain surface or not at all.

I claim:

1. A method of stimulating a neural cell having potentials ranging from a polarized quiescent state to an active depolarized state, the cell active depolarized state having a transmembrane potential substantially different from the quiescent state transmembrane potential, comprising applying a first energy field to the cell to change the cell potential from the quiescent state so the cell transmembrane potential differs from both said states, while the transmembrane potential differs from both said states applying a field including a cyclic magnetic component to the cell, the cyclic magnetic component having a frequency and amplitude and being combined with effects from the first energy field such that each cycle of the cyclic magnetic component causes an incremental change in transmembrane potential of the cell without changing the cell from the quiescent to the active state, applying the cyclic magnetic component to the cell so it has a duration and amplitude and is combined with the effects of the first energy field so there is an accumulation of the incremental changes to change the cell state from the quiescent to the active state.

2. The method of claim 1 wherein the first energy field is derived by applying current to a first coil.

3. The method of claim 2 wherein the current is a unipolar pulse.

4. The method of claim 3 wherein the cyclic magnetic component is derived by supplying a cyclic current to a second coil.

5. The method of claim 3 wherein the cyclic magnetic component is derived by supplying a cyclic current to a second coil while the unipolar pulse current is being applied to the first coil.

6. The method of claim 2 wherein the current includes a series of pulses.

7. The method of claim 2 wherein the current ramps while being applied to the first coil.

8. The method of claim 1 wherein the cyclic magnetic component is derived by supplying a cyclic current to a coil.

9. The method of claim 8 wherein the cyclic current is sinusoidal.

10. The method of claim 8 wherein the cyclic current includes unipolar cyclic pulses.

11. The method of claim 1 wherein the first energy field is derived by applying a first sequence of unipolar current pulses to a first coil.

12. The method of claim 11 wherein the cyclic magnetic component is derived by applying a second sequence of unipolar current pulses to a second coil.

13. The method of claim 1 wherein the first energy field is derived from a source that causes the cell to vibrate.

14. The method of claim 1 wherein the first energy field is derived from an ultrasonic source.

15. The method of claim 1 wherein the first energy field is derived by applying microwave electromagnetic energy to the cell.

16. The method of claim 1 wherein the first energy field is derived by applying a hyperpolarizing magnetic field to a volume of cells surrounding the cell to be stimulated, the cyclic magnetic component being applied to the cell to be stimulated while the cells in the surrounding volume are hyperpolarized, applying the cyclic magnetic component to the cell so the cell is stimulated and applying the magnetic component to the other cells with sufficient intensity to achieve a fired state in the stimulated cell, the applied cyclic magnetic component not having sufficient intensity to achieve the fired state in hyperpolarized cells adjacent the stimulated cell.

17. The method of claim 16 wherein the hyperpolarizing field is derived by simultaneously applying unipolar current to a plurality of different coils having differing locations.

18. The method of claim 17 wherein the cyclic magnetic component is derived by applying current to a flat coil lying in a plane generally at right angles to a surface of a subject including the cell and including an edge in proximity to the surface of the subject, the edge and coil plane being in general alignment with the cell to be stimulated.

19. The method of claim 17 wherein the plural different coils for deriving the hyperpolarizing field comprise first and second coils, and further comprising locating the first and second coils on opposite sides of a third coil for deriving the cyclic magnetic field.

20. The method of claim 19 wherein the cyclic magnetic component is derived by applying current to a flat coil lying in a plane generally at right angles to a surface of a subject including the cell and including an edge in proximity to the surface of the subject, the edge and coil plane being in general alignment with the cell to be stimulated.

21. The method of claim 1 wherein the cyclic magnetic component is asymmetrically coupled to the cell so the magnetic component coupled to the cell has greater amplitude during a first half cycle of the component than during a second half cycle of the component.

22. The method of claim 21 wherein the magnetic component is derived from a magnetic coil energized by an AC source, and vibrating the coil in synchronism with the application of current by the source to the coil to provide the asymmetrical coupling.

23. The method of claim 1 wherein the first energy field changes the cell potential from the quiescent state so the cell transmembrane potential is between the quiescent and active states.

24. The method of claim 1 wherein the first energy field changes the cell potential from the quiescent state so the cell transmembrane potential is not between the quiescent and active states and is closer to the quiescent state than to the active state.

25. The method of claim 1 wherein the first energy field and the cyclic magnetic component are derived by supplying currents to first, second and third coils, each shaped as a flat figure eight coil having approximately equal areas and numbers of series connected turns on opposite sides of a center point.

26. The method of claim 25 further comprising locating the first and second coils in generally parallel planes and the third coil in a plane oblique to the first and second coils.

27. The method of claim 26 further comprising positioning the center points of the first, second and third coils so they respectively coincide with first, second and third lines that extend through and meet at the cell and have differing orientations.

28. The method of claim 25 further comprising supplying synchronized currents to the coils for different intervals.

29. The method of claim 28 wherein the intervals overlap.

30. The method of claim 28 wherein the intervals are sequential.

31. The method of claim 28 wherein the current supplied to one of said coils has positive and negative going segments, the positive going segments having slopes different from the negative going segments so a magnetic field derived from one said coil and coupled to the cell has a greater amplitude during the segment having a larger slope than during the segment having a smaller slope.

32. The method of claim 31 wherein the first, second and third coils have progressively larger areas, the currents supplied to the first, second and third coils being phased so (i) the current supplied to the second coil has a minimum value while the current supplied to the first coil has a peak value and (ii) the current supplied to the third coil has a minimum value while (a) the current supplied to the second coil has a peak value and (b) the current supplied to the first coil has a value about halfway between maximum and minimum values thereof.

33. The method of claim 25 wherein the first, second and third coils have progressively larger areas, the currents supplied to the first, second and third coils being phased so (i) the current supplied to the second coil has a minimum value while the current supplied to the first coil has a peak value and (ii) the current supplied to the third coil has a minimum value while (a) the current supplied to the second coil has a peak value and (b) the current supplied to the first coil has a value about halfway between maximum and minimum values thereof.

34. The method of claim 25 wherein the first, second and third coils have progressively increasing areas, and further comprising locating the first, second and third coils so (a) the center points thereof are aligned and lie on a line extending through the cell, (b) the coils lie in mutually parallel planes, and (c) the first coil is closest to the cell, the third coil is farther from the cell than the first and second coils and the second coil is between the first and third coils.

35. The method of claim 34 wherein the currents in the first, second and third coils are phased and have amplitudes so (a) the magnetic field resulting from current in the third coil tends to cause depolarization of the cell to offset hyperpolarization tendencies of magnetic fields resulting from current in the first and second coils, (b) the magnetic field resulting from current in the first coil causes depolarization of the cell while the magnetic fields resulting from current flowing in the second and third coils tend to offset each other.

36. Apparatus for stimulating a neural cell having potentials ranging from a polarized quiescent state to an active depolarized state, the cell active state having a transmembrane potential substantially different from the quiescent state transmembrane potential, comprising a first source for applying a first energy field to the cell, the first energy field having parameters for changing the cell potential from said quiescent state so the cell transmembrane potential differs from both said states, a second source synchronized with said first source for applying a cyclic magnetic component to the cell while the transmembrane potential differs from both said states, the cyclic magnetic component having a frequency and amplitude and being combined with effects from the first energy field such that each cycle of the cyclic magnetic component causes an incremental change in transmembrane potential of the cell without changing the cell from the quiescent to the active state, the cyclic magnetic component applied to the cell having a duration and amplitude and being combined with effects of the first energy field to cause an accumulation of the incremental changes to change the cell state from the quiescent to the active state.

37. The apparatus of claim 36 wherein the first source for applying the first energy field to the cell includes a first coil.

38. The apparatus of claim 37 wherein the current source is connected to the first coil and derives a current ramp while current is being applied to the first coil.

39. The apparatus of claim 37 where the first coil is connected to a current source.

40. The apparatus of claim 39 wherein the current source derives a series of current pulses.

41. The apparatus of claim 40 wherein the current derived from the cyclic current source includes unipolar cyclic current pulses.

42. The apparatus of claim 36 wherein the first source for applying the first energy field to the cell includes a first coil and a source of pulsed unipolar current connected to the first coil.

43. The apparatus of claim 42 wherein the second source for applying the cyclic magnetic component includes a second coil and a cyclic current source connected to the second coil.

44. The apparatus of claim 42 wherein the second source for applying the cyclic magnetic component includes a cyclic source and second coil connected to the cyclic source while the unipolar current source is connected to the first coil.

45. The apparatus of claim 36 wherein the second source for applying the cyclic magnetic component includes a cyclic current source connected to a coil.

46. The apparatus of claim 45 wherein the cyclic current is sinusoidal.

47. The apparatus of claim 36 wherein the first source for applying the first energy field includes a source of a first sequence of unipolar current pulses connected to a first coil.

48. The apparatus of claim 47 wherein the second source for applying the cyclic magnetic component includes a source of a second sequence of unipolar current pulses connected to a second coil.

49. The apparatus of claim 36 wherein the first source for applying the first energy field includes a source for vibrating the cell.

50. The apparatus of claim 36 wherein the first source for applying the first energy field includes an ultrasonic compressional wave source adapted to apply energy to the cell.

51. The apparatus of claim 36 wherein the first source for applying the first energy field includes a microwave electromagnetic source adapted to apply energy to the cell.

52. The apparatus of claim 36 wherein the first source for applying the first energy field includes a third source for applying a hyperpolarizing magnetic field to a volume of cells surrounding the cell to be stimulated, the second source for applying the cyclic magnetic component being activated while the third source for applying the hyperpolarizing field is activated, the cyclic magnetic component being applied to the cell to be stimulated while being applied to the other cells with sufficient intensity to achieve a fired state in the cell to be stimulated and not having sufficient intensity to achieve the fired state in hyperpolarized cells adjacent the cell to be stimulated.

53. The apparatus of claim 52 wherein the third source for deriving the hyperpolarizing field includes a current source connected so unipolar current is simultaneously applied to plural different coils having differing locations.

54. The apparatus of claim 53 wherein the second source for applying the cyclic magnetic component includes a flat coil adapted to be in a plane generally at right angles to a surface of a subject including the cell and including an edge in proximity to the surface of the subject, the edge and coil plane being in general alignment with the cell to be stimulated.

55. The apparatus of claim 53 wherein the plural different coils for deriving the hyperpolarizing field comprise first and second coils, the apparatus including a third coil for deriving the cyclic magnetic field, the first and second coils being located on opposite sides of the third coil.

56. The apparatus of claim 55 wherein the third coil for deriving the cyclic magnetic component includes a flat coil adapted and arranged to lie in a plane generally at right angles to a surface of a subject including the cell and including an edge in proximity to the surface of the subject, the edge and coil plane being in general alignment with the cell to be stimulated.

57. The apparatus of claim 36 wherein the second source for applying the cyclic magnetic component is arranged so the cyclic magnetic component is asymmetrically coupled to the cell so the magnetic component coupled to the cell has greater amplitude during a first half cycle of the component than during a second half cycle of the component.

58. The apparatus of claim 57 wherein the second source for applying the magnetic component includes a magnetic coil energized by an AC source, and a source for vibrating the coil in synchronism with the application of current by the source to the coil to provide the asymmetrical coupling.

59. The apparatus of claim 36 wherein the first source for applying the first energy field is arranged and adapted to be activated to change the cell from the quiescent state so the cell transmembrane potential is between the quiescent and active states.

60. The apparatus of claim 36 wherein the first source for applying the first energy field is arranged and adapted to be activated to change the cell from the quiescent state so the cell transmembrane potential is not between the quiescent and active states and is closer to the quiescent state than to the active state.

61. The apparatus of claim 36 wherein the first source for applying the first energy field and second source for applying the cyclic magnetic component include first, second and third coils, each shaped as a flat figure eight coil having approximately equal areas and numbers of series connected turns on opposite sides of a center point.

62. The apparatus of claim 61 wherein the first and second coils are located in generally parallel planes and the third coil is located in a plane oblique to the first and second coils.

63. The apparatus of claim 62 wherein the center points of the first, second and third coils are positioned so they respectively coincide with first, second and third lines that extend through and meet at the cell and have differing orientations.

64. The apparatus of claim 61 further including a source for supplying synchronized currents to the coils for different intervals.

65. The apparatus of claim 64 wherein the intervals overlap.

66. The apparatus of claim 64 wherein the intervals are sequential.

67. The apparatus of claim 61 wherein the source for applying the synchronized current is arranged so the current has positive and negative going segments, the positive going segments of the current supplied to one of said coils having slopes different from the negative going segments so a magnetic field derived from said one coil and coupled to the cell has a greater amplitude during the segment having a larger slope than during the segment having a smaller slope.

68. The apparatus of claim 67 wherein the first, second and third coils have progressively larger areas, the source for applying the synchronized current is arranged so the currents supplied to the first, second and third coils are phased so (i) the current supplied to the second coil has a minimum value while the current supplied to the first coil has a peak value and (ii) the current supplied to the third coil has a minimum value while (a) the current supplied to the second coil has a peak value and (b) the current supplied to the first coil has a value about halfway between maximum and minimum values thereof.

69. The apparatus of claim 61 wherein the first, second and third coils have progressively larger areas, the source for applying the synchronized current is arranged so the currents supplied to the first, second and third coils being phased so (i) the current supplied to the second coil has a minimum value while the current supplied to the first coil has a peak value and (ii) the current supplied to the third coil has a minimum value while (a) the current supplied to the second coil has a peak value and (b) the current supplied to the first coil has a value about halfway between maximum and minimum values thereof.

70. The apparatus of claim 61 wherein the first, second and third coils have progressively increasing areas and are located so (a) the center points thereof are aligned and lie on a line extending through the cell, (b) the coils lie in mutually parallel planes, and (c) the first coil is closest to the cell, the third coil is farther from the cell than the first and second coils and the second coil is between the first and third coils.

71. The apparatus of claim 70 wherein the source for supplying the synchronized current is arranged so the currents in the first, second and third coils are phased and have amplitudes so (a) the magnetic field resulting from current in the third coil tends to cause depolarization of the cell to offset hyperpolarization tendencies of magnetic fields resulting from current in the first and second coils, (b) the magnetic field resulting from current in the first coil causes depolarization of the cell while the magnetic fields resulting from current flowing in the second and third coils tend to offset each other.

72. A method of stimulating a neural cell of a subject, the cell having potentials ranging from a polarized quiescent state to an active depolarized state, the cell active depolarized state having a transmembrane potential substantially different from the quiescent state transmembrane potential, comprising placing plural magnetic coils proximate different locations of the subject, energizing the different coils with currents having differing temporal characteristics, the current applied to one of the coils including a cyclic component, magnetic fields resulting from the currents energizing the different coils being coupled to the cell, the magnetic field from at least one other of the coils changing the cell potential from the quiescent state so the cell transmembrane potential differs from both said states, the cyclic component being applied to the cell while the transmembrane potential differs from both said states, the cyclic magnetic component having a frequency and amplitude and being combined with effects from the magnetic field from said at least one other coil such that each cycle of the cyclic magnetic component causes an incremental change in transmembrane potential of the cell without changing the cell from the quiescent to the active state, the cyclic magnetic component applied to the cell having a duration and amplitude and being combined with the effects of the magnetic field from said at least one other coil to cause an accumulation of the incremental changes to change the cell state from the quiescent to the active state without changing other cells from the quiescent to the active state.

73. A method of stimulating a neural cell having potentials ranging from a polarized quiescent state to an active depolarized state, the cell active depolarized state having a transmembrane potential substantially different from the quiescent state transmembrane potential, comprising applying a first energy field to the cell with a first excitation transducer, applying a second energy field to the cell with a second excitation transducer spatially displaced from the first excitation source, the first and second energy fields causing interacting activities in the cell, the interacting activities changing the cell transmembrane potential from the polarized quiescent state to another polarization state different from the polarized quiescent state.

74. The method of claim 73 wherein the first and second energy fields are initially applied to the cell at different times.

75. The method of claim 73 wherein one of the energy fields has a cyclic component.

76. The method of claim 73 wherein both of the energy fields have cyclic components.

77. The method of claim 73 wherein one of the energy fields has a ramping component.

78. The method of claim 73 wherein both of the energy fields have ramping components.

79. Apparatus for stimulating a neural cell having potentials ranging from a polarized quiescent state to an active depolarized state, the cell active state having a transmembrane potential substantially different from the quiescent state transmembrane potential, comprising plural transducers for applying plural energy fields to the cell, the plural transducers adapted to have different positions relative to the cell, plural excitation sources for connection with the plural transducers, the transducers and the excitation sources having a capability to be positioned and arranged so the plural energy fields cause interacting activities in the cell, the interacting activities changing the cell transmembrane potential from the polarized quiescent state to another polarization state different from the polarized quiescent state.

* * * * *